United States Patent [19]

Gianferante

[11] Patent Number: 5,292,302
[45] Date of Patent: Mar. 8, 1994

[54] ARTICULATING SPLINT

[76] Inventor: Mark L. Gianferante, 11421 NW. 39 St., Sunrise, Fla. 33323

[21] Appl. No.: 802,496

[22] Filed: Dec. 5, 1991

[51] Int. Cl.$^5$ ............................................. A61F 5/04
[52] U.S. Cl. ........................................ 602/13; 602/15; 602/16; 602/20; 602/26
[58] Field of Search ............... 602/5, 6, 12, 15, 16, 602/20, 21, 23, 26, 13

[56] References Cited

U.S. PATENT DOCUMENTS

| | | |
|---|---|---|
| 2,092 | 5/1841 | Douglass . |
| 19,025 | 1/1858 | Gruol . |
| 21,872 | 10/1858 | Bunce . |
| 31,501 | 2/1861 | Whitter .................... 602/15 |
| 158,894 | 1/1875 | Bissell ....................... 602/15 |
| 163,829 | 5/1875 | Westerkamp ............. 602/15 |
| 504,218 | 8/1893 | Hoppe ....................... 602/16 |
| 552,143 | 12/1895 | Rankin . |
| 649,237 | 5/1900 | Dyson . |
| 1,089,201 | 3/1914 | Swanson ................... 602/15 |
| 1,334,596 | 3/1920 | Crouch ...................... 602/6 |
| 2,339,515 | 1/1944 | Parcher ..................... 128/84 |
| 2,827,897 | 3/1958 | Pawlowski ................ 602/16 |
| 3,745,997 | 7/1973 | Gledhill .................... 602/15 |
| 3,943,923 | 3/1976 | Scheinberg ............... 602/6 |
| 4,050,456 | 9/1977 | Cornue ..................... 128/88 |
| 4,169,467 | 10/1979 | Rabischong et al. ..... 602/13 X |
| 4,209,011 | 6/1980 | Peck et al. ................ 602/19 |
| 4,266,298 | 5/1981 | Graziano ................. 602/13 X |
| 4,270,527 | 6/1981 | Peters et al. ............. 602/13 |
| 4,854,305 | 8/1989 | Bremer ..................... 602/32 |
| 5,000,168 | 3/1991 | Lipson ...................... 602/20 |

Primary Examiner—Robert A. Hafer
Assistant Examiner—Brian E. Hanlon
Attorney, Agent, or Firm—Lorusso & Loud

[57] ABSTRACT

This invention relates to splints and the method of manufacturing these splints for first aid or emergency rescue use, and has particular reference to an improved hinge and pivot splint having angular adjustment and securing devices.

9 Claims, 7 Drawing Sheets

ARTICULATING SPLINT

BACKGROUND OF THE INVENTION

1. Field of the Invention

This invention relates generally to splints for first aid or emergency rescue use, and has particular reference to an improved hinge and pivot splint having angular adjustment and securing means.

2. Description of the Prior Art

There have been hinge and pivot splints developed in the past, however most are for surgical use, used only on a single body part, and require professional experience to apply to a patient.

In the prehospital setting it is particularly important to splint the injured body part, whether it be the knee, arm, shoulder, ankle or back, in the exact position in which it is found. Should the body part position be changed there is the danger that both the blood vessels and the nerves within and surrounding the injured body part will be damaged.

In the past, splints for emergency use have consisted of two side pieces placed on both sides of a limb. The side pieces are braced together and the desired angle is set by means of a screw.

A more recent development has been the use of a set of splints for both leg and arm injuries. U.S. Pat. No. 2,339,515 discloses the use of two dissimilar contoured sections, one having a crutch-type end portion, clamped together through the means of a bolt. The splint sections can be fixed in alignment or at relative angles up to 90°. In order for the splint to be used on both the leg and the arm, a more comprehensive set of splint sections with increased lengths are necessary.

In other recent developments, splint devices include members which are angularly as well as linearly adjustable. These splints have limited orientation settings. It is also necessary to bolt the planar members together through individual or continuous slots. The securement of the members in a particular position is cumbersome, time consuming and may require personnel specifically trained in those mechanisms. In addition, these devices are not easily adjustable.

Additional operating problems arise with the use of the conventional splint. The paramedic or other emergency worker must carry additional instruments needed to construct the splint, i.e., additional pieces to lengthen the splint for it to conform to different parts of the body, the necessary nuts and bolts to adjust and tighten the particular angle, and a tool for the actual tightening of the bolts. Additional storage space is also needed. There is also the danger that the pieces may be lost, or not within the immediate vicinity when needed. In addition, it is difficult for one person to both adjust the angle needed, and maintain the angle while tightening the bolts.

It is therefore an object of the present invention to provide an improved splint for the immobilization of straight and non-straight skeletal injuries in the prehospital emergency setting.

It is another object of the present invention to provide a splint for use with all body parts.

It is yet another object of the present invention to provide a splint which offers vastly improved stabilization while minimizing injury manipulation and maximizing patient comfort.

It is yet another object of the present invention to provide a splint which can be adjusted, applied, and secured in a minimum amount of time by a single person.

It is a further object of the present invention to provide a splint which can be simply constructed, readily accessible, and easily stored.

It is still a further object of the present invention to provide a splint which allows an operating range of nearly 270 degrees.

SUMMARY OF THE INVENTION

The problems of the prior art are greatly resolved by the device of the present invention which consists of a splint device for immobilizing skeletal injuries in the emergency setting. The splint is constructed so that it can be quickly and easily applied t the patient by one person. The splint offers vastly improved stabilization and accessibility while minimizing injury manipulation and maximizing patient comfort. The splint folds to a compact size for easy storage.

The invention features two embodiments of splints including a pivot splint and a hinge splint. The most apparent applications of the splints are for the involvement of the shoulder, elbow, knee and ankle, but they can be used as a common straight splint, and less commonly for certain angulated shaft fractures and crushing injuries to the foot.

Common attributes of both models of the present invention consist of an all non-metallic construction permitting radio translucency, meaning decreased manipulation of the injury because the splints may remain employed throughout various radiation procedures.

Each splint contains two main members, the main members each comprising a radio-translucent upper and lower active surface having therapeutic movement, and an active surface restraining means. The main members are connected by an articulating means. In the hinge splint, the articulating means consists of a hingedly fixed member which provides for vertical planar restrictive movement of the main members. In the pivot splint, the articulating means consists of a pivot point which provides for horizontal planar restrictive movement of the main members.

Each embodiment contains means for fixedly establishing an angle between the main members. In the hinge splint, a linkage arm is hingedly fixed to the lower active surface of each member, and a lock link is hingedly fixed to each linkage arm. In the pivot splint, a brace member is pivotally connected to one end of a main member.

One of the keys to this invention consists of the means for securing the angle formed by the linkage arms and lock links in the hinge embodiment, or the brace member in the pivot embodiment. The securing means consists of the position affixation of two members. Such securing means is attached to each main member, the linkage arms and lock links and the brace member.

Each embodiment contains hook and loop straps connected to each main member to assure the immobilization of the injured portion of the body. In addition, a pneumatic pillow may be spread across each upper active surface, giving full conformation to the body.

BRIEF DESCRIPTION OF THE DRAWINGS

The invention will be more fully understood by reading the following description in conjunction with the figures described below in which like reference numbers refer to like members.

DETAILED DESCRIPTION OF THE PREFERRED EMBODIMENTS

Figure 1:
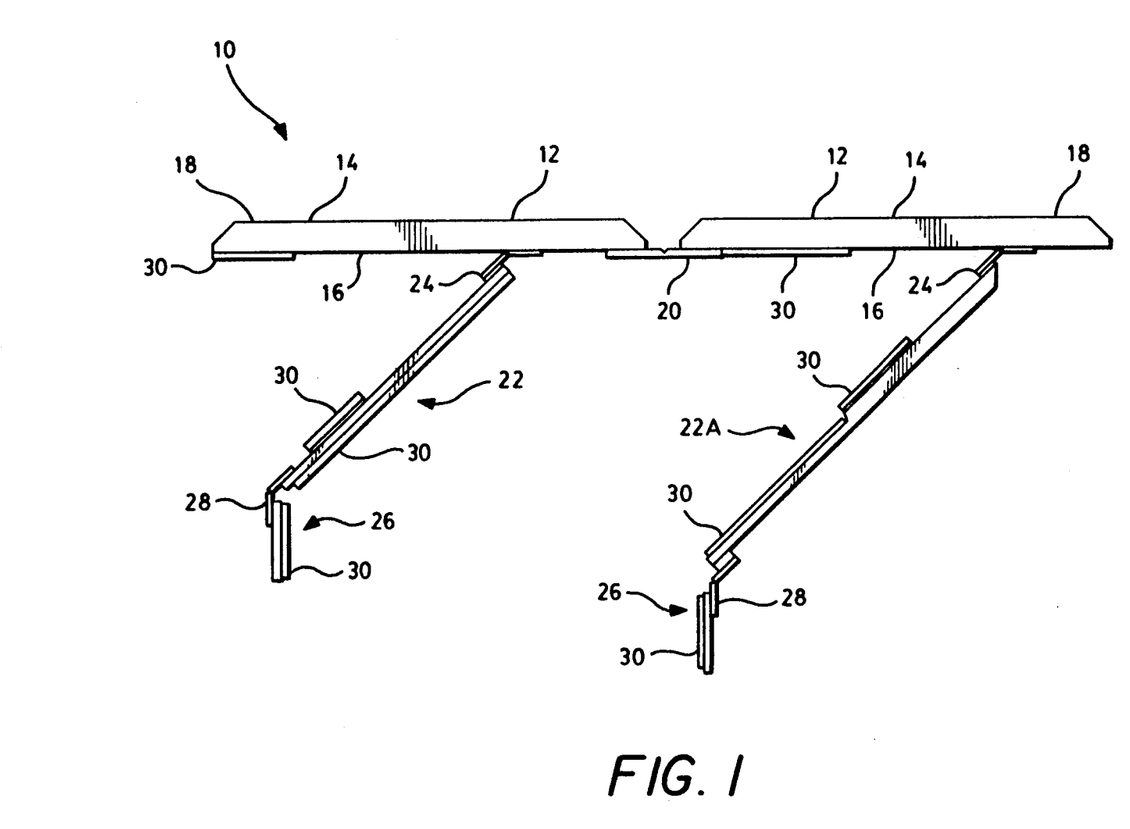
FIG. 1 is a right side elevational view of one form of splint illustrative of an embodiment of the invention.
Figure 10:
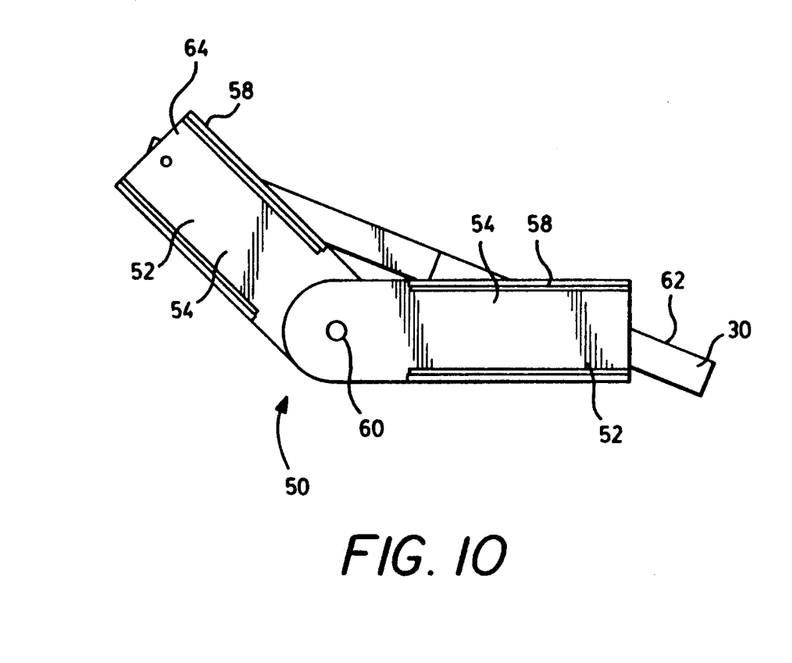
FIG. 10 is a right side elevation view of the pivot splint device of the present invention.

Referring to the drawings, in FIGS. 1 and 10 there is shown a splint device for use in an emergency setting. Emergency means the prehospital, hospital, or extra hospital setting; this term includes such applications as ambulatory, camping, mountain or sea rescue or military field applications.

In FIG. 1 there is shown a hinge splint, a feature unit of the invention, which will be generally referred to by reference number 10. In FIG. 10 there is shown an alternative embodiment, referred to herein as a pivot splint and referred to by reference number 50.

Each splint, 10 and 50, consists of two main members, 12, and 52, respectively. Each main member is constructed from a radio-translucent rigid material.

Radio-translucent is a term describing the density of the material comprising the splint device to either ionizing or nonionizing radiation. In either type of radiation, radio-translucent is a density that will not obscure resolution or imaging of an injured portion of a patient wearing a splint device beyond that which will prevent diagnosis of an injury that would otherwise be determinable absent the splint device. Therefore, there will be decreased manipulation of the injury because the splints need not be removed for diagnosis. The invention, however, does not expect or require any single material to be radio translucent to x-rays, NMRs and sonograms. Ionizing radiation includes all x-ray emissions such as Positron Emersion Tomography (PET), Computerized Axial Tomography (CAT), standard hard and soft x-rays and others. Nonionizing radiation includes magnetic radiation, Nuclear Magnetic Resonance (NMR), sound (Sonograms) and others. It is also understood that even if the radiation is obscured to a detectable degree, if computer or other enhancement techniques including mechanical filters or lengthened exposures are capable of overcoming this effect, sufficient radio-translucence is present.

Rigid, as used to describe the main member, is used in relation to the injury immobilization objective clearly encompassed in this invention. In the instance of splints as applied to compound bone fractures, it is contemplated that the fractured bone ends will not be displaced from the relative positions initially fixed by application of the splint. It is to be understood that some tortion may occur in such application but such is still included in the term rigid.

Each main member, additionally, contains an upper 14, 54 and lower 16, 56 (FIG. 11) active surface. The upper active surface 14, 54 is used in relation to the present invention to mean the base fixable in alignment with the remedially desired position in which to immobilize the injured portion of a patient and remains in direct contact with this injured portion.

The lower active surface 16, 56 is used in relation to the present invention to describe a face which lies under the upper active surface. The lower active surface, just as with the upper active surface, serves to immobilize the injured portion of the patient.

Upon the upper active surface, 14, 54 there is an active surface restraining means. The active surface restraining means is used in relation to the injury immobilization objective of this invention. The active surface restraining means prevents the injured portion of a patient from disengaging from the upper active surface of the splint. In the instance of fracture, the fractured bone ends will not be displaced from the relative positions initially fixed by application of the splint as fastened by active surface restraining means. It is to be understood that some tortion may occur in such application.

In one embodiment bed-defining rails, 18, 58 (FIG. 6C) are employed as active surface restraining means. Bed-defining rails are projections which extend from and above the edge of the main member and continue generally along such edge to define a recess or bed. Examples of such bed-defining rails include cradles, cups, and covers of boxes. In the instance of splints, the bed-defining rails of the upper active surface can be a cup shaped delineation or a tapering shape.

The main members, 12 and 52, are joined together in order to provide for articulation of the main members. Depending on the particular splint, the articulation of the main members will be restricted in either vertical or horizontal movement. In FIG. 1, the hinge splint 10 comprises a hingedly fixed articulating means 20 for vertical planar restrictive movement of the main members. Vertical planar restrictive movement is the movement of the main members in relation to each other, which is restricted to movement in a vertical plane.

In FIG. 10, the pivot splint 50 comprises a pivot point articulating means 60 for horizontal planar restrictive movement of the main members. Horizontal planar restrictive movement is the movement of the main members in relation to each other, which is restricted to movement in a horizontal plane.

Each splint, 10 and 50, also contains a means for fixedly establishing an operating angle between the main members, 12 and 52, respectively. The operating angle is the angle by which the splint is applied to the body. In FIG. 1, the means for fixedly establishing an angle in a hinge splint consists of a pair of linkage arms 22 and 22a. Each linkage arm comprises a rigid and rectangular planar member. In one embodiment, the linkage arms 22 and 22a are fixedly established by hinges 24 to the lower active surface. Additionally, a pair of lock links 26 are connected by hinges 28 to the linkage arms 22 and 22a. The lock links 26 each comprise a rigid and rectangular planar member. Together, the linkage arms 22 and 22a and lock links 26 construct the desired angle for the injured portion of the patient's body.

In one embodiment, one linkage arm 22a is relatively longer than the other. The different lengths of the linkage arms 22 and 22a provide for four different configurations of the linkage arms. The configurations provided in FIGS. 2 through 5 demonstrate the splint's operating range of nearly 270° about a vertical plane.

Figures 2, 3:
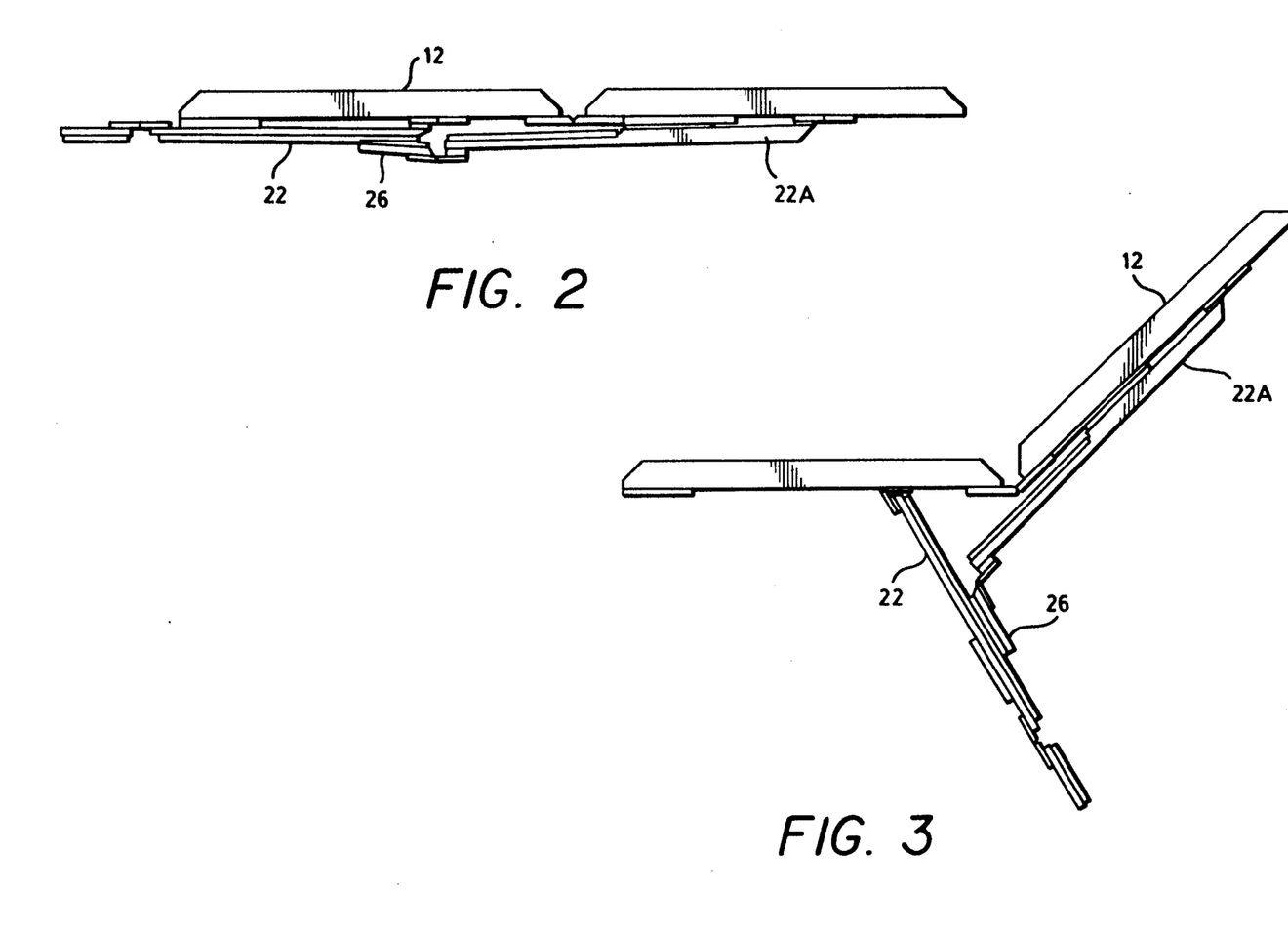
FIG. 2 is a right side elevational view of the splint device of FIG. 1 in its 180° operating range.
FIG. 3 is a right side elevation view of the splint device of FIG. 1 in its 90°-180° operating range.

FIG. 2 shows the hinge splint's configuration in the 180° range. Both the short linkage arm 22 and long linkage arm 22a are locked to their main members 12, and the long linkage arm's lock link 26 is locked to the short linkage arm 22. Suggested uses of this configuration are for any application where a medium length straight splint would be desired.

FIG. 3 shows the hinge splint's configuration in the 90° to 180° range. The long linkage arm 22a is locked to its main member 12, and the short linkage arm 22 is locked to the long linkage arm lock link 26. Suggested uses of this configuration are for injuries involving the foot, including the ankle, and the arm, including the elbow, where the pivot splint would aggravate injury.

Figure 4:
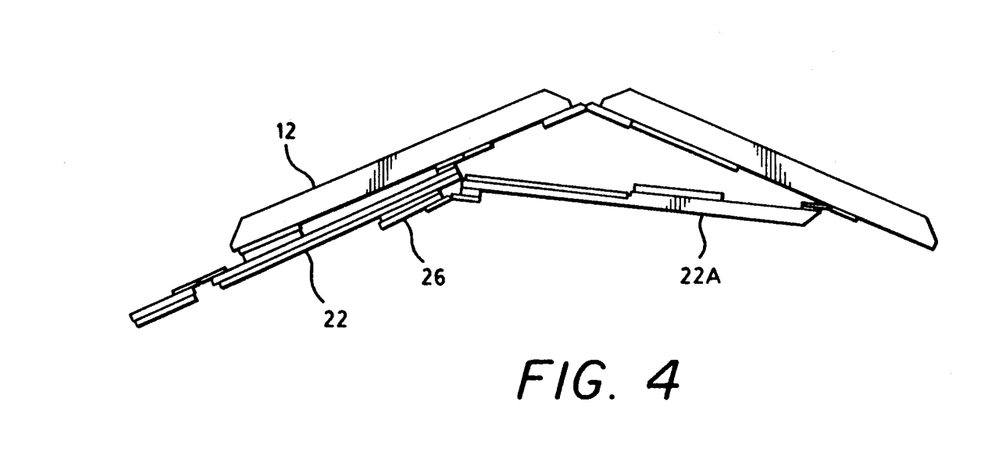
FIG. 4 is a right side elevation view of the splint device of FIG. 1 in its 180°-270° operating range.

FIG. 4 shows the hinge splint's configuration in the 180° to 270° range. The short link arm 22 is locked to its main member 12, and the long linkage arm lock link 26 is locked to the short linkage arm 22. Suggested uses include under the knee for injuries involving the lower extremities when stabilization in the flexed position is required, and under the arm when shoulder girdle injuries require stabilization in the raised position is desired.

Figure 5:
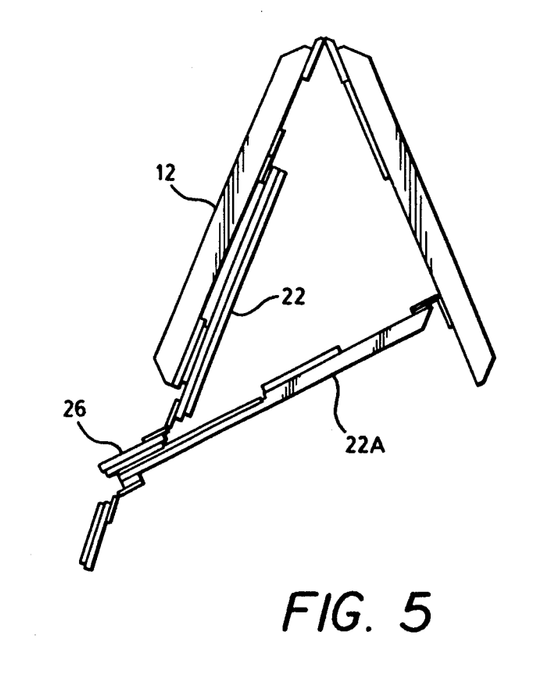
FIG. 5 is a right side elevation view of the splint device of FIG. 1 in its 270°-330° operating range.

FIG. 5 shows the hinge splint's configuration in the 270° to 330° range. The short linkage arm 22 is locked to its main member 12 and the short linkage arm's 22 lock link 26 is locked to the long linkage arm 22a. Suggested use is for injuries involving the shoulder when stabilization of the arm below the plane of the shoulder is required.

Since the hinge splint has such an extensive range of travel, the splint can be used to immobilize injuries involving ankles, feet, knees, elbows and shoulders. It can be adjusted and applied in a minimum amount of time, and offers vastly improved stabilization and accessibility while minimizing injury manipulation and maximizing patient comfort.

In FIG. 10, the means for fixedly establishing an angle in a pivot splint consists of a brace member 62 pivotally connected to one end 64 of a main member 52. The brace member 62 consists of a rigid rectangular planar member. The brace member can be rotated or pivoted about the main member in order to construct the desired angle for the injured portion of the patient's body.

The primary application for the pivot splint is for behind the arm or forearm when the elbow or near to the elbow injury is present. It can also be employed at the lower extremity in the same fashion, but the hinge splint is usually a better choice because of usual horizontal positioning of injured legs.

The upper 14, 54 and lower 16, 56 active surfaces of the hinge and pivot splint, respectively FIG. 1 and FIG. 10, are fixed in conjunction with each other in a therapeutic fashion. Fixed in a therapeutic fashion, in reference to the active surfaces, means the manner in which the surfaces are secured causing both a straight and a bent joint on a patient to remain immobile. In the instance of a fractured knee, the active surfaces can be fixedly established (and the knee consequently immobilized) in an unbent (180° angle) or at a bent (90° angle) position or any other angle desired.

One of the key aspects to this invention is the means by which the operating angle is secured. The securing means is the position affixation of two members of the splint. Engaging surfaces include Velcro, a Trademark of Velcro, magnets, and mechanically operated devices.

In one embodiment, an interlocking mechanism is used. This mechanism consists of rows of nodules which interlock with nodules of a similar surface when the two surfaces are joined. This system is commercially available as "Dual Lock Fastener". The Dual Lock Fastener is similar in use to velcro in that it pushes together, and pulls apart at any area across its surface. However, it offers a much stronger holding strength and doesn't allow any free slack in shear or tensile loads within its holding capacity.

Figure 11:
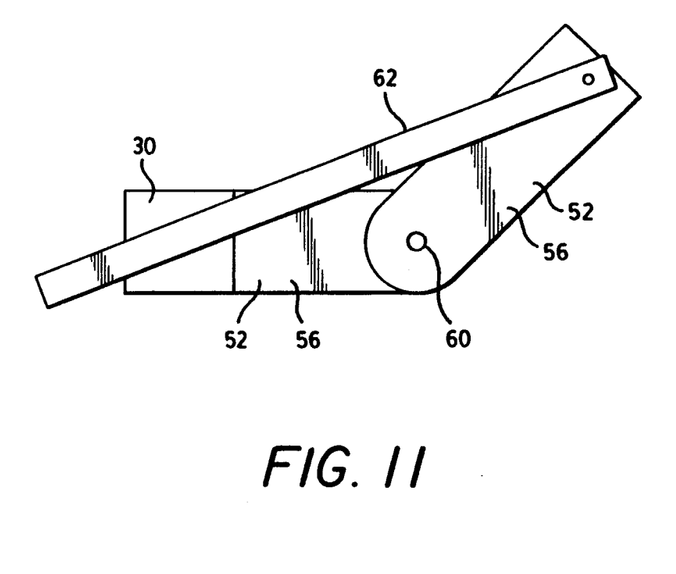
FIG. 11 is a left side elevation view of the pivot splint device of FIG. 10.

In one embodiment, as shown in FIG. 1, the securing means 30 is placed on each main member 12, linkage arm 22, 22a and lock link 26. In FIG. 11, the securing means 30 is shown on one of the main members 52. In FIG. 10, the securing means 30 is shown on the brace member 68.

FIGS. 6 through 9, show one embodiment of the upper active surface opposition means. The upper active surface opposition means consists of an integral strap system for the hinge and pivot splint for securing the straps to the injured portion of the body. As shown in FIG. 6a, hooks 80 are attached along one side of the main member 12, and along the opposite side of the main member are loop straps 82, as shown in FIG. 6b. FIG. 6c shows a cross section of the hook and loop straps, taken across segment A—A in FIGS. 6a and 6b, respectively, represented with pneumatic pillows 90 placed on the upper active surface 14, 54.

Figure 6A:
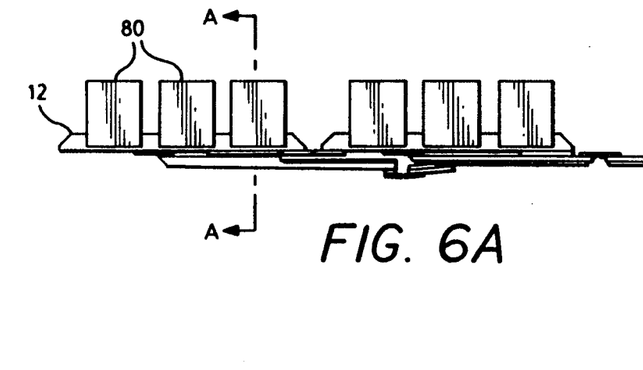
FIG. 6a is a side view of the splint device of FIG. 1 with accompanying hook.
Figure 6B:
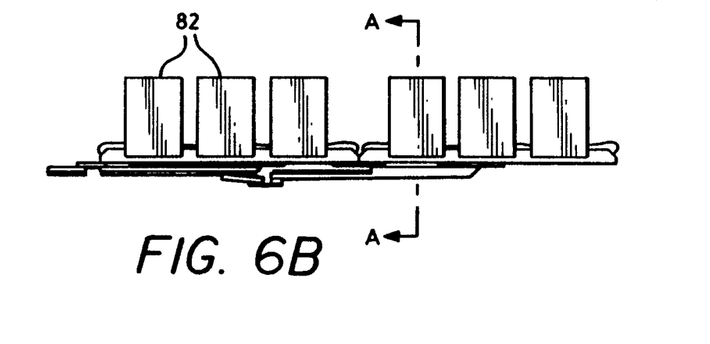
FIG. 6b is a side view of the splint device of FIG. 1 with accompanying loop straps.

In one embodiment, as shown in FIGS. 6a and 6b, the hook 80 and loop straps 82 are made from velcro, a product of Velcro. The hooks are ultrasonically welded continuously along one side of the active surface restraining means, with the loop strap ultrasonically welded to the other side. In another embodiment, there are three 2" wide loop straps on each main member.

In yet another embodiment, the hinge splint's integral straps will fit upper and lower extremities, except for thighs on the most obese, and will only require ace bandages for those thighs or for securing to the trunk of a patient when immobilizing a shoulder.

The straps may be partly released while still maintaining immobilization, and allowing visual examination of that part of the extremity. The straps may also be deployed to secure dressings to soft tissue injuries in the area.

Figure 7A:
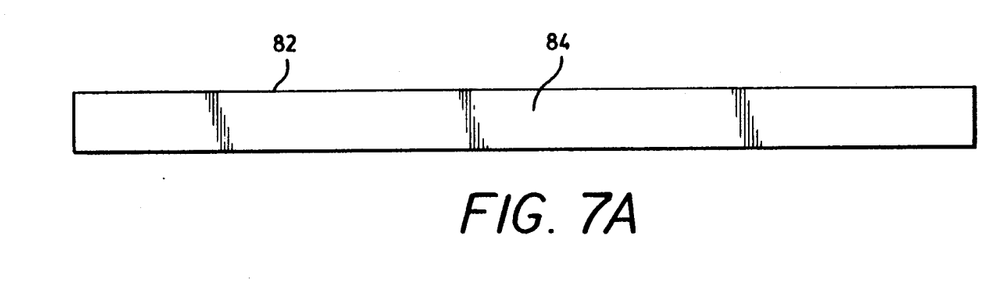
FIG. 7a is a bottom elevation view of the loop strap of the splint device of FIGS. 1 and 10.
Figure 7B:
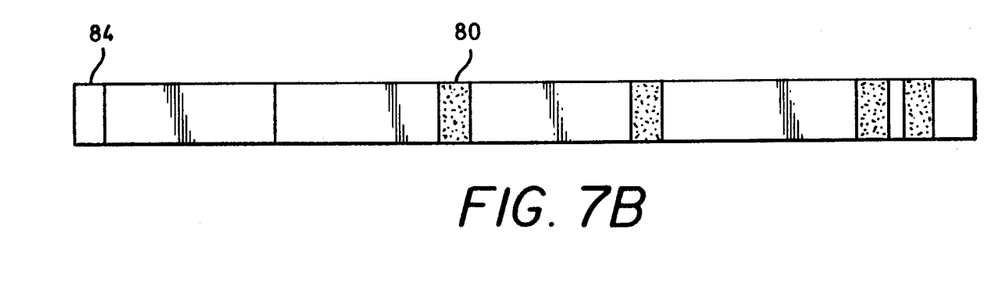
FIG. 7b is a top elevation view of the loop strap of the splint device of FIG. 1 and 10.
Figure 8:
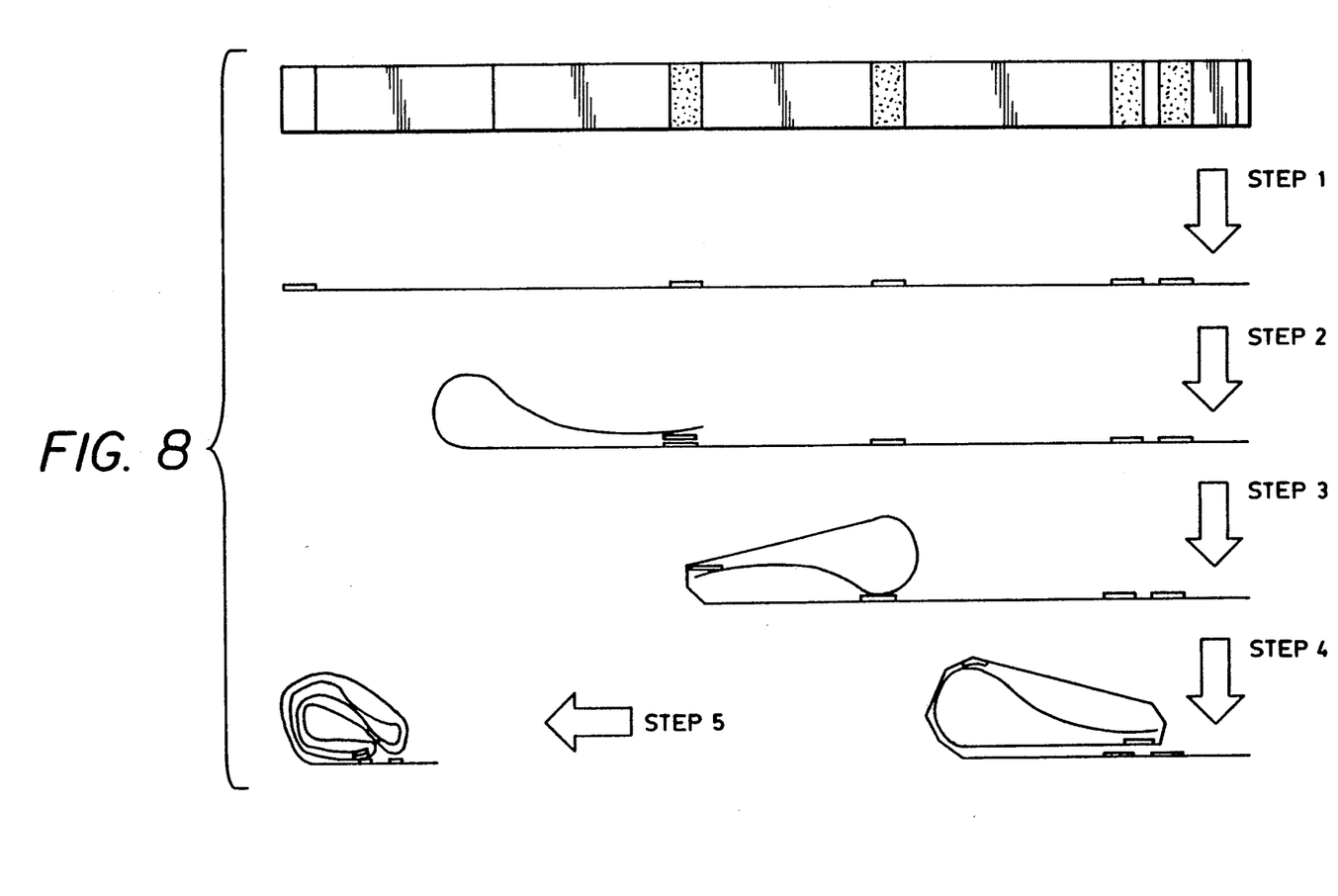
FIG. 8 is a graphic representation of steps to form the storable strap of the splint device of FIG. 1 and FIG. 10.

In another embodiment, the loop straps are easily storable. As shown in FIG. 7a, the lower surface 84 of the loop strap 82 consists of a woven strip of loop fastener material. Loop fastener material is comprised of a plurality of plyable rings. As shown in FIG. 7b, the upper surface consists of the storage system. The storage system is comprised of segments of woven strips of hook fastener material 80, and loop fastener material 84. Hook fastener material is comprised of a plurality of stiff nodules. The hook and loop fastener materials are fastened together to enable the loop strap to be folded upon itself and remain folded, as shown in steps 1 through 5 of FIG. 8. The loop straps, as folded, allow for easy storage without the use of external fasteners, such as ties or knots to remain compact.

Figures 6C, 9B:
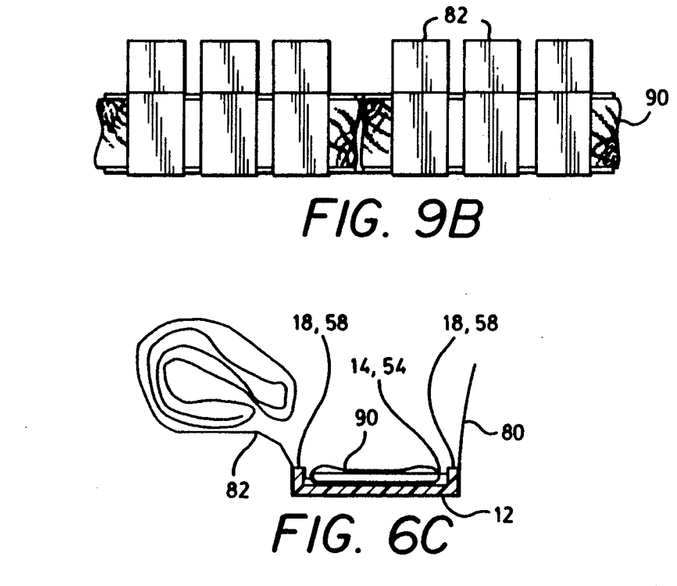
FIG. 6c shows a cross section of a side view of the hook and loop straps, as shown taken across segment A—A in FIGS. 6a and 6b, respectively.
FIG. 9b is a top elevation view of the splint device of FIG. 1 with accompanying pneumatic pillow and strap system after the loop strap has been laid across the upper surface of the pneumatic pillow.
Figure 9A:
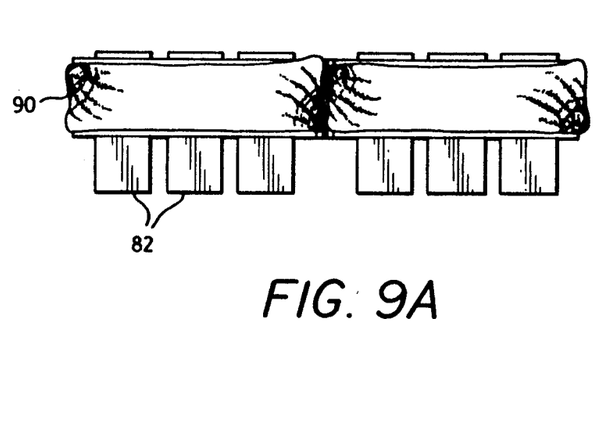
FIG. 9a is a top elevation view of the splint device of FIG. 1 with accompanying pneumatic pillow and strap system.

In one embodiment as shown in FIGS. 9a and 9b, pneumatic pillows 90 are placed on the upper active surface resulting in a newly formed upper active surface. The pillows 90 eliminate point loads with contact pressure being evenly spread across the entire contact area giving full conformation to the body. The pillows 90 are carefully filled with a fixed volume of air, so that in case of failure immobilization will not be compromised. As shown in FIG. 9a, the loop straps are affixed on one side of the upper active surface and are subsequently laid across the upper surface of the pneumatic pillow, as shown in FIG. 9b, to result in the immobilization of the injured portion of the body.

It should be understood that the above description pertains to but one of several embodiments which make use of the present invention. Accordingly, an individual ordinarily skilled in the art will realize additional applications for the present invention. The invention is to be defined, therefore, not by the preceding description but by the claims that follow.

What is claimed is:

1. An emergency splint device comprising:
   first and second main members, each of said main members comprising
     an elongated rigid radio-translucent member having upper and lower active surfaces;
     projections upstanding from longer sides of said radio-translucent members to form in conjuction with said upper active surfaces first and second beds for receiving body parts;
   said main members being pivotally connected to each other at ends thereof;
   arm means pivotally connected to at least one of said main members for fixedly establishing an angle between said main members;
   securing means fixed to at least one of said main members and to said arm means, and said main member securing adapted to interlock with said arm securing means, for securing said arm means to said at least one of said main members at locations removed from said pivotal connection of said arm means to said at least one of said main members, for locking said at least one of said main members at said angle; and strap means fixed to said upper active surface and adapted to attach said main members to said body parts.

2. The splint device according to claim 1 wherein said pivotal connection between said main members comprises a hinge;
   said arm means comprises
     (i) a pair of linkage arms, each comprising a rigid and quadrilateral planar member hingedly connected to said lower active surface of one of said main members; and
     (ii) a pair of lock links, each comprising a rigid rectangular planar member hingedly connected at an end thereof to a free end of one of said linkage arms; and
   said securing means being affixed on each of said main members, each of said linkage arms and each of said lock links.

3. The splint device according to claim 1 wherein said pivotal connection between said main members comprises a pivot point connection which restricts the main members to horizontal planar restrictive movement; said arm means for fixedly establishing an angle between said main members comprises a brace member consisting of a rectangular planar member pivotally connected to one end of said first main member for planar movement about said pivotal connection to said first main member; and; said securing means being affixed on said lower surface of said second main member and on said brace member.

4. The splint device according to claim 1 wherein said securing means comprises strips of hermaphroditic material.

5. The splint device according to claim 1 wherein pillows are disposed on said upper active surfaces of said main members.

6. The splint device according to claim 5 wherein said pillows are pneumatic pillows which provide substantial conformation to said body parts.

7. The splint device according to claim 1 wherein said splint device is constructed of material which is radio-translucent to ionizing radiation.

8. The splint device according to claim 1 wherein said splint device is constructed of material which is radio-translucent to nonionizing radiation.

9. The splint device according to claim 1 wherein said arm means comprises first and second arms, said securing means fixed to said arm means comprises first and second securing means which are fixed, respectively, to said first and second arm means and adapted to interlock with each other.

* * * * *

UNITED STATES PATENT AND TRADEMARK OFFICE
CERTIFICATE OF CORRECTION

PATENT NO. : 5,292,302
DATED : March 8, 1994
INVENTOR(S) : Mark L. Gianferante

It is certified that error appears in the above-indentified patent and that said Letters Patent is hereby corrected as shown below:

Title on cover page, first column, after [54] delete "ARTICULATING SPLINT" and insert -- ARTICULATING EMERGENCY SPLINT--;

Col. 1, line 2, delete "ARTICULATING SPLINT" and insert --ARTICULATING EMERGENCY SPLINT--;

Col. 7, line 46, after "securing" insert --means--.

Signed and Sealed this

First Day of November, 1994

Attest:

BRUCE LEHMAN

*Attesting Officer*      *Commissioner of Patents and Trademarks*